United States Patent

Thiebes et al.

(10) Patent No.: US 6,884,899 B2
(45) Date of Patent: Apr. 26, 2005

(54) PREPARATION OF 1-AMINO-4-HYDROXYANTHRAQUINONES

(75) Inventors: Christoph Thiebes, Köln (DE); Josef-Walter Stawitz, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 217 days.

(21) Appl. No.: 10/219,795

(22) Filed: Aug. 15, 2002

(65) Prior Publication Data

US 2003/0045735 A1 Mar. 6, 2003

(30) Foreign Application Priority Data

Aug. 16, 2001 (DE) .......................... 101 40 107

(51) Int. Cl.[7] .............................................. C09B 1/20
(52) U.S. Cl. ............................. 552/243; 552/245
(58) Field of Search ................... 552/243, 245

(56) References Cited

U.S. PATENT DOCUMENTS

| 1,931,264 A | | 10/1933 | Meuly | 260/59 |
| 2,419,405 A | | 4/1947 | Klein | 260/380 |
| 3,507,606 A | | 4/1970 | Hildreth et al. | 8/39 |
| 3,654,319 A | * | 4/1972 | Neeff | 552/248 |
| 4,309,221 A | * | 1/1982 | Neeff et al. | 106/493 |

FOREIGN PATENT DOCUMENTS

| DE | 2 041 374 | | 2/1972 |
| GB | 914453 | * | 1/1963 |
| GB | 2013701 | | 8/1979 |

* cited by examiner

*Primary Examiner*—Barbara P. Badio
(74) *Attorney, Agent, or Firm*—Diderico van Eyl; Jennifer R. Seng; Jill Denesvich

(57) ABSTRACT

The present invention relates to a process for preparing 1-amino-4-hydroxyanthraquinones of the formula (I)

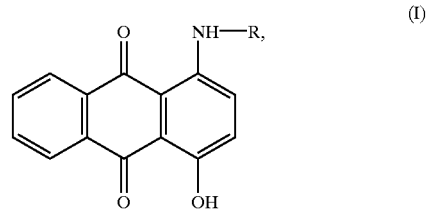

wherein R is an aliphatic or aromatic radical, by reacting 1,4-dihydroxyanthraquinone, optionally as a mixture with 2,3-dihydro-1,4-dihydroxyanthraquinone, with aliphatic or aromatic amines in the presence of N-methyl-2-pyrrolidone.

8 Claims, No Drawings

PREPARATION OF 1-AMINO-4-HYDROXYANTHRAQUINONES

BACKGROUND OF THE INVENTION

The invention relates to a process for preparing 1-amino-4-hydroxy-anthraquinones and to the use of the compounds thus prepared for mass coloration of plastics.

1-Amino-4-hydroxyanthraquinones are known, for example, as dyes for plastics and synthetic fibers and also as intermediates for preparing wool dyes. These compounds have hitherto been prepared by reacting 1,4-dihydroxyanthraquinone (quinizarin), optionally mixed with 2,3-dihydro-1,4-dihydroxyanthraquinone (leucoquinizarin), with amines in the presence or absence of condensation assistants.

In U.S. Pat. No. 1,931,264, for instance, bis-adduct formation is suppressed by use of an aqueous solvent, but at the same time excess amine is needed to obtain good yields. In GB-A 2,013,701, the reaction is carried out in the presence of surfactants. DE-A-161 96 46 and U.S. Pat. No. 2,419,405 describe the use of alcohols as a solvent.

Disadvantages common to all of these processes are the low space-time yield and the fact that the dye obtained is not sufficiently brilliant.

It is an object of the present invention to provide a process that is free of the disadvantages of the prior art.

SUMMARY OF THE INVENTION

This object has been found to be achieved by a process for preparing 1-amino-4-hydroxyanthraquinones of formula (I)

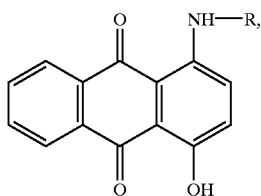

(I)

wherein R is an aliphatic or aromatic radical, comprising reacting 1,4-dihydroxyanthraquinone, optionally as a mixture with 2,3-dihydro-1,4-dihydroxyanthraquinone, with aliphatic or aromatic amines in the presence of N-methyl-2-pyrrolidone.

DETAILED DESCRIPTION OF THE INVENTION

The preferred aliphatic or aromatic amines used in the process according to the invention are primary amines. The aliphatic amines can be, for example, saturated or unsaturated, branched or straight chain. Particularly preferred aliphatic amines are, for example, those of the following formulas:

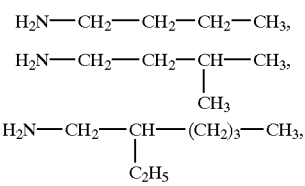

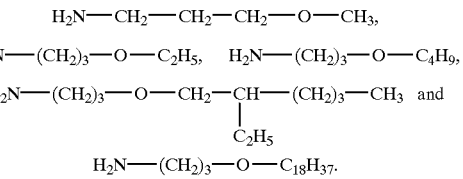

However, the process according to the invention is particularly useful for preparing 1-arylamino-4-hydroxyanthraquinones in which the aromatic amines are primary and which conform in particular to the formula (II)

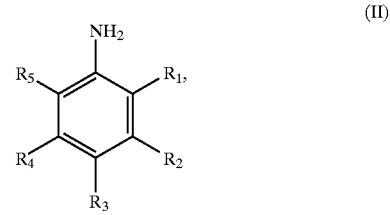

(II)

where $R_1$, $R_3$, $R_4$, and $R_5$ are independently H, $C_1$–$C_{12}$-alkyl (especially $C_1$–$C_4$-alkyl), halogen, $C_1$–$C_4$-alkoxy, or $C_6$–$C_{10}$-aryloxy, and $R_2$ is H, $C_1$–$C_{12}$-alkyl (especially $C_1$–$C_4$-alkyl), halogen, $C_1$–$C_4$-alkoxy, $C_6$–$C_{10}$-aryloxy, or —$SO_2$—NH—$R_6$, where $R_6$ is optionally substituted aryl (especially $C_6$–$C_{10}$-aryl, such as phenyl or naphthyl) or alkyl (especially $C_1$–$C_4$-alkyl, such as methyl, ethyl, propyl, or butyl), wherein the substituents are preferably selected from $C_1$–$C_4$-alkyl, OH, halogen, $C_1$–$C_4$-alkoxy, and $C_9$–$C_{10}$-aryloxy.

Particular preference is given to the following aromatic amines of the formula (II): aniline, o-toluidine, 3,5-dimethylaniline, 2,4-dimethylaniline, p-toluidine, and p-aminoacetanilide.

The 1,4-dihydroxyanthraquinone (quinizarin) used in the process according to the invention is preferably used in a mixture with its leuco form, 2,3-dihydro-1,4-dihydroxyanthraquinone (leucoquinizarin), wherein the leuco compound is preferably used in an amount of 1 to 90% by weight (preferably 1 to 20% by weight and particularly preferably 3 to 10% by weight), based on the sum total of quinizarin and leucoquinizarin. The mixture of leucoquinizarin and quinizarin can be formed, for example, in situ from the quinizarin by addition of reducing agents such as zinc dust or sodium dithionite, but the anthraquinone compounds quinizarin and its leuco form can also be prepared separately.

The ratio of amine to anthraquinone compound (i.e., total amount of quinizarin and leucoquinizarin) is preferably selected so that there are 1 to 2 mol equivalents (particularly preferably 1.1 to 1.3 mol equivalents) of amine per mole of anthraquinone (total amount of quinizarin and leucoquinizarin).

In a particularly preferred embodiment, the process according to the invention is carried out in the presence of boric acid. Boric acid is preferably used in an amount of 0.025 to 1 mol equivalent (especially 0.025 to 0.4 mol equivalent), based on the amount of anthraquinone (total amount of quinizarin and leucoquinizarin).

The process can optionally be carried out in the presence of further organic solvents, especially NMP-miscible organic solvents. Suitable solvents are, for example, aliphatic alcohols, such as n-butanol or isoamyl alcohol, or water. Excess amine can also be used as an organic solvent. The amount of further solvents, especially water, can account, for example, for 1 to 30% by weight of the reaction mixture, but preferably no further solvent is used. The amount of NMP based on the total amount of the reaction mixture is preferably 30 to 75% by weight and especially 40 to 55% by weight.

The process according to the invention is preferably carried out at a temperature of 60 to 160° C., preferably at 70 to 130° C. and especially at 85 to 105° C.

Water can be added to the reaction mixture, and water is also formed by the reaction. Water can be partly removed during the reaction, for example, by distillation. It is preferable to proceed in such a way that the reaction melt after the reaction has ended contains 1 to 10% by weight (especially 2 to 3% by weight) of water.

In a preferred embodiment of the process according to the invention, boric acid and an auxiliary acid are used. Auxiliary acids used are, for example, inorganic or organic acids, especially hydroxycarboxylic acids.

The hydroxycarboxylic acids that are preferably used are preferably aliphatic or aromatic. In a particular embodiment of the process according to the invention, the aliphatic hydroxycarboxylic acids bear the hydroxyl and carboxyl groups on the same carbon atom. Aromatic hydroxycarboxylic acids preferably bear the hydroxyl and carboxyl groups on two immediately adjacent aromatic carbon atoms.

Preferred aliphatic hydroxycarboxylic acids have 2 to 7 carbon atoms. Examples that can be mentioned are hydroxyacetic acid, lactic acid, malic acid, tartaric acid, citric acid, 2,2-bis(hydroxymethyl)propionic acid, and galactonic acid. Particular preference is given to hydroxyacetic acid and also lactic acid.

Important aromatic hydroxycarboxylic acids are especially ortho-hydroxycarboxylic acids of benzene or of naphthalene. Preference is given to salicylic acids and derivatives thereof, for example, aliphatic esters, such as $C_1$–$C_4$-alkyl esters, or aromatic esters, such as $C_6$–$C_{10}$-aryl esters, of the formula

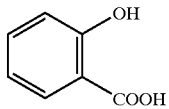

and also naphthalene-ortho-hydroxycarboxylic acids and derivatives thereof, for example, aliphatic esters, such as $C_1$–$C_4$-alkyl esters, or aromatic esters, such as $C_6$–$C_{10}$-aryl esters, of the formula

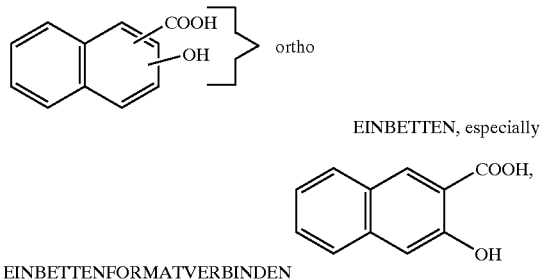

EINBETTENFORMATVERBINDEN which are optionally substituted by one or more identical or different R radicals, where R is H, $C_1$–$C_4$-alkyl (especially $CH_3$, halogen, especially Cl, Br and F, OH, CN, COOH, or $NO_2$. Examples that can be mentioned are 2,5-dihydroxy-1,4-benzenedicarboxylic acid and 2-naphthol-3-carboxylic acid.

The process according to the invention can be carried out in the presence of one or more hydroxycarboxylic acids.

The reaction mixture after the reaction has ended is preferably cooled. To oxidize any leuco compounds present, air can be passed through the reaction mixture. However, the oxidation can also be carried out with oxidizing agents other than oxygen. Preferably, no oxidation is carried out. This is generally followed by the isolation of the anthraquinone compound of the formula (I), generally by precipitating the anthraquinone compound of the formula (I) with aliphatic alcohols such as methanol, ethanol, propanol, or butanol or with water or alcohol mixtures. The anthraquinone compound is filtered and preferably washed with the alcohols mentioned. This is generally followed by washes with water and finally drying. An advantage of the process according to the invention is that the desired products are obtained in excellent yields and qualities even without precipitation with an aliphatic alcohol and/or water.

The process according to the invention is notable for an excellent space-time yield and also for improved products.

The dyes prepared by the process according to the invention are particularly useful for mass coloration of plastics.

Mass coloration as used herein is meant to apply especially to processes in which the dye is incorporated into the molten plastic material, for example by means of an extruder or where the dye is added to starting components for preparing the plastic, for example, to monomers, prior to the polymerization.

Particularly preferred plastics are thermoplastics, for example, vinyl polymers, polyesters, polyamides, and polyolefins, especially polyethylene and polypropylene, or polycarbonates.

Suitable vinyl polymers are polystyrene, styrene-acrylonitrile copolymers, styrene-butadiene copolymers, styrene-butadiene-acrylonitrile terpolymers, polymethacrylate, polyvinyl chloride, and others.

Also suitable are polyesters such as, for example, polyethylene terephthalates, polycarbonates, and cellulose esters.

Preference is given to polystyrene, styrene interpolymers, poly-carbonates, polymethacrylates, and polyamides. Particular preference is given to polystyrene, polyethylene, and polypropylene.

The high molecular weight compounds mentioned can be present individually or in mixtures, as plastically deformable materials, or as melts.

The dyes obtained by the process according to the invention are preferably used in finely divided form, for which dispersants can but need not be used.

If the dye mixture is added after the polymerization, it is preferably dry mixed or ground with the granular plastic before this mixture is plasticated and homogenized, for example, on mixing rolls or in screws. But it is also possible to add the dyes to the liquid melt and homogeneously disperse the latter by stirring. The material thus precolored is then further processed in a conventional manner, for example by spinning to form bristles, filaments, and the like or by extrusion or injection molding to form shaped articles.

Since the dyes are stable to polymerization catalysts, especially peroxides, it is also possible to add the dye to the monomeric starting materials for the plastics and then to polymerize in the presence of polymerization catalysts. To this end, the dye is preferably dissolved in or intimately mixed with the monomeric components.

The dyes obtained by the process according to the invention are preferably used for dyeing the stated polymers in amounts of from 0.0001 to 1% by weight and especially 0.01 to 0.5% by weight based on the amount of polymer.

By adding pigments that are insoluble in the polymers (for example, titanium dioxide), it is possible to obtain corresponding useful hiding colorations. Titanium dioxide can be used in an amount of 0.01 to 10% by weight and preferably 0.1 to 5% by weight based on the amount of polymer.

The coloration process according to the invention provides transparent or hiding brilliant violet colorations having good thermal stability and also good light, weather, and sublimation fastness.

The coloration process according to the invention can also utilize mixtures of the dyes of the formula (I) with other dyes and/or inorganic or organic pigments.

The nonlimiting examples which follow illustrate the invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and parts and percentages are by weight.

EXAMPLES

Example 1

1-p-Toluidino-4-hydroxyanthraquinone:

A 1000 ml 4-neck flask was charged with 271 parts (1.13 mol) of quinizarin, 17 parts (0.07 mol) of dihydroquinizarin, 157 parts (1.47 mol) of p-toluidine, 4 parts (0.065 mol) of boric acid, 4.5 parts of water, and 35.5 parts (0.355 mol) of 90% lactic acid in 413 parts of N-methylpyrrolidone with vigorous stirring. The mixture was heated to 90° C. and maintained at 90° C. for 12 h, after which it was cooled down and filtered. The product obtained was washed with 500 parts of hot methanol at 60° C. and dried, leaving 370 parts (94% yield) of a dark violet product that provided a very bright violet when used for coloring polystyrene.

Example 2

1-Anilino-4-hydroxyanthraquinone:

Example 1 was repeated, except that the 157 parts of p-toluidine were replaced by 136 parts (1.46 mol) of aniline. This provided 312 parts (83% yield) of a dark violet product that gave a violet hue when used for coloring polystyrene. The hue had a similar color strength to the dye described in Example 1 but was distinctly redder.

Example 3

1-p-Acetamidoanilino-4-hydroxyanthraquinone:

Example 1 was repeated, except that the 157 parts of p-toluidine were replaced by 220 parts (1.47 mol) of p-aminoacetanilide and 600 parts of NMP were used instead of 400 parts. This provided 312 parts of a dark violet product that yielded a very bright violet when used for coloring polystyrene. The hue had a similar color strength to the dye described in Example 1 but was somewhat more bluish.

Example 4

1-(3',5'-Dimethylanilino)-4-hydroxyanthraquinone:

Example 1 was repeated, except that the 157 parts of p-toluidine were replaced by 178 parts (1.47 mol) of 3,5-dimethylaniline. This provided 336 parts of a dark violet product that yielded a very bright violet when used for coloring polystyrene. The hue had a similar color strength to the dye described in Example 1 but was somewhat more reddish and brighter.

What is claimed is:

1. A process for preparing 1-amino-4-hydroxyanthraquinones of the formula (I)

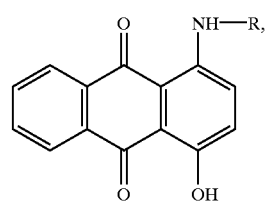

(I)

wherein R is an aliphatic or aromatic radical, comprising reacting 1,4-dihydroxyanthraquinone, optionally as a mixture with 2,3-dihydro-1,4-dihydroxyanthraquinone, with an aliphatic or aromatic amine in the presence of N-methyl-2-pyrrolidone.

2. A process according to claim 1 wherein the amine is an aromatic amine.

3. A process according to claim 1 wherein the amine is an aromatic amine having the formula (II) wherein

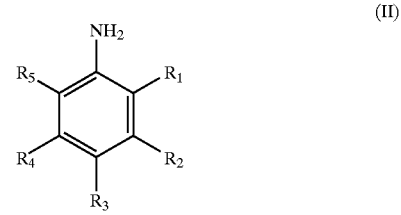

(II)

$R_1$, $R_3$, $R_4$ and $R_6$ are indepently H, $C_1$–$C_{12}$-alkyl, halogen, $C_1$–$C_4$-alkoxy, or $C_6$–$C_{10}$-aryloxy, and $R_2$ is H, $C_1$–$C_{12}$-alkyl, halogen, $C_1$–$C_4$-alkoxy, $C_8$–$C_{10}$-aryloxy, or —$SO_2$—NH—$R_8$, where $R_8$ is optionally substituted aryl or alkyl.

4. A process according to claim 3 wherein $R_6$ is $C_8$–$C_{10}$-aryl substituted with $C_1$–$C_4$-alkyl, OH, halogen, $C_1$–$C_4$-alkoxy, or $C_9$–$C_{10}$-aryloxy or is $C_1$–$C_4$-alkyl.

5. A process according to claim 1 wherein the aromatic amine is aniline, o-toluidine, 3,5-dimethylaniline, 2,4-dimethylaniline, p-toluidine, or p-aminoacetanilide.

6. A process according to claim 1 wherein the reaction is carried out in the presence of boric acid.

7. A process according to claim 1 wherein the reaction is carried out in the presence of an auxiliary acid.

8. A process according to claim 7 wherein the auxiliary acid is a hydroxycarboxylic acid.

* * * * *